United States Patent [19]

Boutevin et al.

[11] Patent Number: 4,633,004

[45] Date of Patent: Dec. 30, 1986

[54] FLUOROSILANES AND PROCESS FOR THEIR PREPARATION

[75] Inventors: Bernard Boutevin, Montpellier; Yves Pietrasanta, Meze, both of France

[73] Assignee: Atochem, France

[21] Appl. No.: 797,002

[22] Filed: Nov. 12, 1985

[30] Foreign Application Priority Data

Nov. 13, 1984 [FR] France ................. 84 17279

[51] Int. Cl.$^4$ ............ C07F 7/08; C07F 7/10; C07F 7/18
[52] U.S. Cl. .................... 556/419; 556/422; 556/427; 528/30
[58] Field of Search ............ 556/419, 422, 427; 528/30

[56] References Cited

U.S. PATENT DOCUMENTS

| | | | |
|---|---|---|---|
| 3,678,089 | 7/1972 | Berger | 556/422 X |
| 3,716,517 | 2/1973 | Pittman et al. | 556/422 X |
| 3,772,346 | 11/1973 | Hess | 556/427 X |
| 3,794,672 | 2/1974 | Kim | 556/427 |
| 3,809,783 | 5/1974 | Pittman et al. | 556/422 X |
| 3,903,123 | 9/1975 | Deiner et al. | 556/422 X |

*Primary Examiner*—Paul F. Shaver
*Attorney, Agent, or Firm*—Brooks, Haidt, Haffner & Delahunty

[57] ABSTRACT

Fluorosilanes containing at least one partially or totally fluorinated chain and at least one silicon chain linked with a thioether bridge, the fluorosilanes being prepared by radical addition of a silicon thiol to a fluorinated olefin, and the fluorosilanes being useful intermediates for the preparation of fluorinated silicones such as fluorinated silicone elastomers.

10 Claims, No Drawings

FLUOROSILANES AND PROCESS FOR THEIR PREPARATION

BACKGROUND OF THE INVENTION

The present invention relates to silanes, and more particularly, it relates to novel fluorosilanes used to produce fluorinated silicones and to processes for the preparation of such fluorosilanes.

The elastomers of fluorosilicones, among which the most frequently encountered are the derivatives of poly(trifluoropropylmethylsiloxane) having the structure:

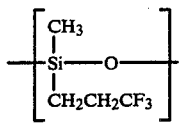

are known for their stability over a large temperature range and their excellent resistance to chemical agents, to liquid fuels, to oils, and to solvents. Moreover, with respect to other fluorinated elastomers, these fluorinated silicones retain a good level of properties at extreme temperatures. These properties, and above all the solvent resistance, arise from the carbon-fluorine chemical bond.

There are a number of patents relating to the synthesis of fluorinated silicones or to those fluorosilanes which can be used for their preparation. These fluorosilanes have on a silicon atom at least one group permitting later polycondensation (particularly a chlorine atom or an alkoxy group) and are generally obtained by the hydrosilylation of fluorinated olefins in the presence of a catalyst, usually hexachloroplatinic acid or one of its derivatives, according to the reaction:

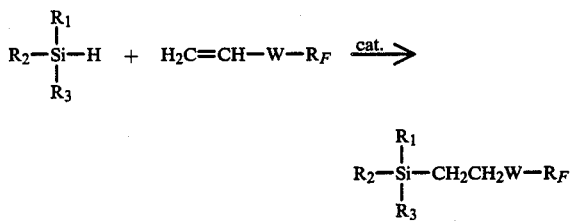

wherein $R_1$, $R_2$, and $R_3$ represent groups, at least one of which permits later polycondensation to silicone, $R_F$ is a fluorinated chain, and W is a direct linkage or a divalent linkage, for example, by an ether group, an ester group, an amide, a sulfonamide, a urethane, and the like. These can be seen, for example, in British Pat. No. 869,343, and U.S. Pat. Nos. 3,012,006 and 3,422,131. Unfortunately, this hydrosilylation reaction is often difficult to carry out in practice except in the case of allylic derivatives, such as $(CF_3)_2$—CH—O—$CH_2CH=CH_2$.

U.S. Pat. No. 3,794,672 shows fluorosilanes having the formula:

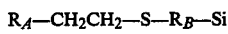

$R_A$—$CH_2CH_2$—S—$R_B$—Si wherein $R_A$ is a perfluoroalkyl radical having from one to four carbon atoms and $R_B$ is an alkylene radical also having one to four carbon atoms. These fluorosilanes are obtained by the radical reaction of an olefin having the formula $R_ACH=CH_2$ on a silicon thiol having the formula:

HS—R—Si

The Chemical Abstracts 93, 99 (1980), no. 73717u abstract mentions compounds similar to those in U.S. Pat. No. 3,794,672 but obtained by the reaction of a fluorinated thiol and a vinylsilane.

THE INVENTION

It has been found that new fluorosilanes can be prepared according to the present invention. These fluorosilanes are generally represented by the formula:

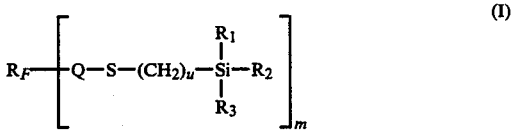

wherein $R_1$ is a halogen atom or an alkoxy group; $R_2$ and $R_3$ are each a hydrogen or a halogen atom, an alkoxy group, an alkyl group or an aryl group; u is two or three; m is one or two; $R_F$ is a partly or totally fluorinated radical; and Q is a divalent group containing at least one oxygen atom. These fluorosilanes according to the invention are obtained by the simple radical addition of a silicon thiol to a fluorinated olefin.

In certain preferred embodiments of the invention, $R_1$ is chlorine, an alkoxy group having one or two carbon atoms, or phenyl, and $R_2$ and $R_3$ are alkyl groups having one or two carbon atoms or phenyl.

The preferred thiol for use in the practice of this invention is a 3-mercaptopropylsilane having the formula:

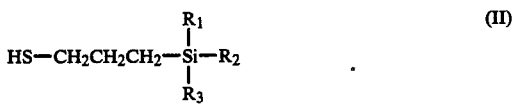

wherein $R_1$, $R_2$, $R_3$ have the same meaning as previously stated. A wide range of fluorinated olefins can be used in the practice of this invention. In certain desirable embodiments of the invention, the following ether olefins are used:

$R'_f$—$CH_2CH_2$—O—$CH_2$—CH=$CH_2$ (III)

$R'_f$—$CH_2CH_2$—O—$CH_2$—$C_6H_4$—CH=$CH_2$ (IV)

(V)

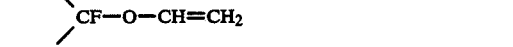

(VI)

$R'_f$—O—CF=$CF_2$ (VII)

The following ester olefins are used:

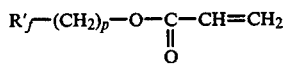 (VIII)

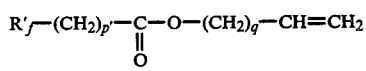 (IX)

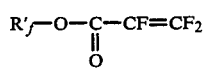 (X)

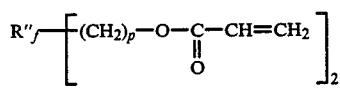 (XI)

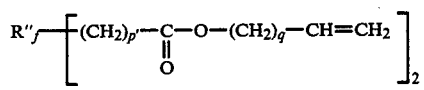 (XII)

and the following amide olefins are used:

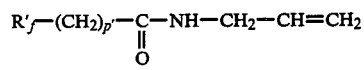 (XIII)

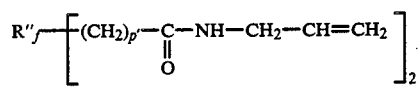 (XIV)

 (XV)

 (XVI)

In the foregoing formulas, $R'_f$ is a $C_xF_{2x+1}$ radical, $R''_f$ is a $C_xF_{2x}$ radical, X is a fluorine or chlorine atom, p is an integer from two to 18, p' is an integer from zero to ten, and q is an integer from zero to nine. In these formulas, x is an integer from two to 20, and in preferred embodiments, x is four to 16.

The addition reaction can be carried out in an aprotic organic vehicle or solvent, such as, for example, a nitrile like acetonitrile, butyronitrile, isobutyronitrile, and the like; an amide such as dimethylformamide and the like; an ether such as tetrahydrofuran and the like; an aromatic hydrocarbon such as benzene and the like; or a halogenated hydrocarbon such as chloroform, carbon tetrachloride, and the like. The reaction is generally carried out at a temperature of from 30° to 100° C. under a nitrogen sweep. In certain preferred embodiments, the reaction is carried out at a temperature of from 60° to 80° C.

To initiate the reaction, the usual radical initiators such as diazoic derivatives like azobis-isobutyronitrile and the like; peroxides such as benzoyl peroxide and the like; hydroperoxides such as tert-butyl hydroperoxide and the like; and percarbonates can be used. The quantity of the initiator can be varied over a wide range. It is generally desirable that an initiator be used in an amount from 0.005 to 0.1 moles per mole of the thiol used. In certain preferred embodiments, the quantity of initiator with respect to the thiol is from 0.01 to 0.05 moles per mole.

The fluorosilanes with a thioether bridge according to the invention are valuable intermediates for the preparation of silicone elastomers. Depending upon the number of hydrolyzable groups, such as halogen atoms or alkoxy groups, fixed on the silicon, they can be utilized either to build polysiloxane chains or as transfer agents or as cross-linking agents.

Unless otherwise stated herein, all parts, percentages, proportions and ratios are by weight.

The following Examples are given to illustrate embodiments of the invention as it is presently preferred to practice it. It will be understood that these Examples are illustrative, and the invention is not to be considered as restricted thereto except as indicated in the appended claims.

EXAMPLE I

Addition of dimethoxymethyl-3-mercaptopropylsilane to allyl-1,1,2,2-tetrahydroperfluorooctyl ether A mixture containing 10 ml acetonitrile; $2.5 \times 10^{-2}$ moles of the ether $C_6F_{13}$—$CH_2CH_2$—O—$CH_2$—$CH=CH_2$; $2.6 \times 10^{-2}$ moles of silane $(CH_3O)_2Si$—$(CH_3)CH_2CH_2CH_2SH$, and $0.5 \times 10^{-3}$ moles of azobis-isobutyronitrile (AIBN) is heated for four hours at 80° C. under a nitrogen atmosphere. After distillation of the reaction mixture, there are obtained 12.4 g of an addition product having the formula:

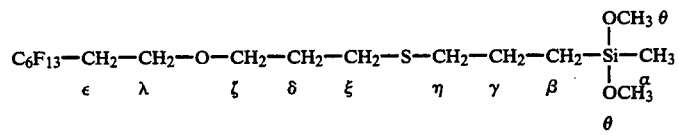

where the nuclear magnetic resonance (NMR) spectrum for hydrogen shows the following peaks in parts per million:

| | |
|---|---|
| 0 | the CH₃ singlet, α |
| 0.62 | the poorly resolved triplet of CH₂, β, with the two H atoms, γ |
| 1.57 | a quintuplet of CH₂, γ, with the four protons, η and β |
| 1.75 | the other quintuplet of CH₂, δ, with the four protons, ξ and ζ |
| 2.3 | the detripled triplet of CH₂, ε, with the CF₂ and the two protons, λ |
| 2.44 | the triplet of CH₂, η, with the two protons, γ |
| 2.48 | the triplet of CH₂, ξ, with the two protons, δ |
| 3.4 | the six protons of OCH₃ groups, θ |
| 3.45 | a triplet of CH₂, ζ, with the two protons, δ |
| 3.6 | a triplet of CH₂, λ, with the two protons, ε |

The fluorinated allylic ether utilized in this Example can be prepared as follows:

A flask fitted with cooling and provided with a mechanical agitator rotating at 500 rpm is charged with a mixture containing $7.7 \times 10^{-2}$ moles of the alcohol $C_6F_{13}$—$CH_2CH_2OH$; 80 ml of a 50% soda solution; 2.6 g of tetrabutylammonium hydrogen sulfate, and 0.385 moles of allyl chloride. The mixture is kept at 42° C. for six hours. Thereafter, the reaction mixture is diluted with 20 ml of methylene chloride and washed a number of times with water. After evaporation of the solvent and distillation of the residue under vacuum, a 95% yield of allylic ether having the formula $C_6F_{13}CH_2CH_2-O-CH_2-CH=CH_2$, boiling at 76° C. under 20 torr, is obtained.

EXAMPLE II

Addition of dimethoxymethyl-3-mercaptopropylsilane to fluorinated ether olefin

A flask is charged with 24 g ($5\times10^{-2}$ mole) of

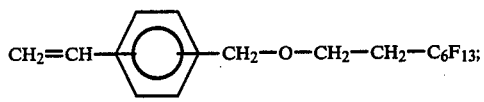

9 g ($5\times10^{-2}$ mole) of dimethoxymethyl-3-mercaptopropylsilane; and 0.25 g ($1.5\times10^{-3}$ mole) of AIBN in 100 ml of acetonitrile. The mixture is heated at 80° C. for four hours under a nitrogen stream. After evaporation of the solvent, 31 g of a viscous liquid corresponding to the addition product:

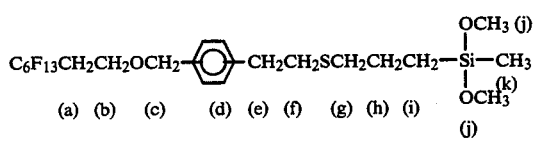

is obtained.

Proton NMR shows the following peaks, with the shifts in parts per million:

| | | |
|---|---|---|
| (a) | 2.35 | detripled triplet of $CH_2$ triplet by $CF_2$ and detripled by $CH_2$ |
| (b) | 3.75 | triplet with the 2'H (a) |
| (c) | 4.5 | singlet |
| (d) | 7.4–7.6 | multiplet |
| (e) | 2.5 | triplet with the two protons (f) |
| (f) | 2.3 | triplet with the two protons (e) |
| (g) | 2.44 | triplet with the two protons (h) |
| (h) | 1.6 | quintuplet with the two protons (g) and the two protons (i) |
| (i) | 0.62 | poorly resolved triplet with the two protons (h) |
| (j) | 3.48 | singlet |
| (k) | 0.1 | singlet. |

EXAMPLE III

Addition of dimethoxymethyl-3-mercaptopropylsilane to fluorinated methacrylate

A flask is charged with acetonitrile under a nitrogen sweep; 4.32 g ($10^{-2}$ mole) of fluorinated methacrylate having the formula

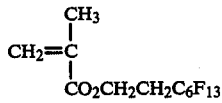

and 18 g ($10^{-1}$ mole) of dimethoxy-3-mercaptopropylsilane with 0.05 g ($3\times10^{-4}$ mole) AIBN. After four hours reaction at 80° C., a viscous liquid is obtained which gives a gas phase chromatographic principal peak and some peaks of lesser importance in a decreasing quantity corresponding to the adducts of higher order. By evaporation of the solvent, a product of the general formula

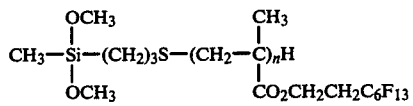

is obtained by distillation under vacuum. The mono adduct which distills at 98° C. under $10^{-2}$ torr is obtained by the distillation under vacuum.

NMR analysis of the compound:

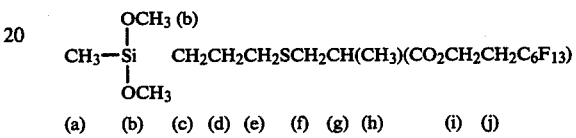

shows the following NMR shifts in parts per million:

| | | |
|---|---|---|
| (a) | 0.09 | singlet |
| (b) | 3.48 | singlet |
| (c) | 0.65 | poorly resolved triplet with the protons (d) |
| (d) | 1.62 | quintuplet with the two protons (c) and the two protons (e) |
| (e) | 2.65 | triplet with the two protons (d) |
| (f) | 2.55 and 2.8 | two undoubled doublets attributable to (g) and (f) |
| (g) | 2.5 | sextuplet; part x of the system ABx (protons f and h) |
| (h) | 1.2 | doublet with the proton (g) |
| (i) | 4.4 | triplet of $CH_2$ (j) |
| (j) | 2.5 | detripled triplet of $CF_2$ and $CH_2$ (j) |

EXAMPLE IV

Addition of dimethoxymethyl-3-mercaptopropylsilane to different fluorinated allyls of the general formula:
R—$CH_2$—$OCH_2CH=CH_2$ In the foregoing formula, R is $CF_3$ (a); ($CF_2$—CF—Cl)$_2$Cl (b); and ($CF_2$)$_2$H (c).

A flask is charged with $5\times10^{-2}$ moles of dimethoxy-3-mercaptopropylsilane and $5\times10^2$ moles of R—$CH_2$—$OCH_2$—$CH=CH_2$ and $1.5\times10^{-3}$ moles of AIBN in 50 ml of acetonitrile at 80° C. under a nitrogen sweep. After four hours of reaction, the mono adducts are obtained in excellent yield by evaporation of the solvent.

Proton NMR shows the following mono adducts:

(a')

| $CF_3$ | $CH_2$ | O | $CH_2$ | $CH_2$ | $CH_2$ | S | $CH_2$ | $CH_2$ | $CH_2$ | Si(OCH$_3$)$_2$ | (CH$_3$) |
|---|---|---|---|---|---|---|---|---|---|---|---|
| $3.8\times10^{-6}$ | $3.52\times10^{-6}$ | | $1.8\times10^{-6}$ | $2.5\times10^{-6}$ | $2.56\times10^{-6}$ | | $1.62\times10^{-6}$ | $0.65\times10^{-6}$ | | $3.5\times10^{-6}$ | $0.1\times10^{-6}$ |
| (quad) | (t) | | (quint) | (t) | (t) | | (quint) | (t) | | (s) | (s) |

-continued

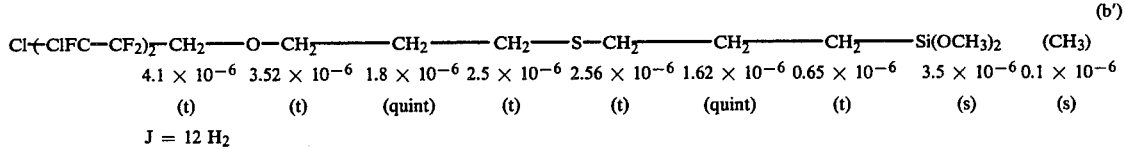

(b')

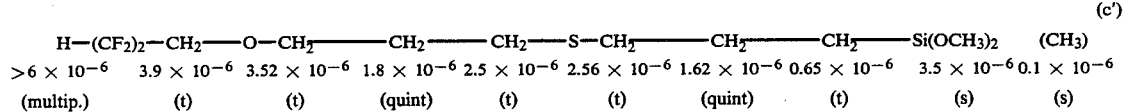

(c')

What is claimed is:

1. Fluorosilanes having the formula:

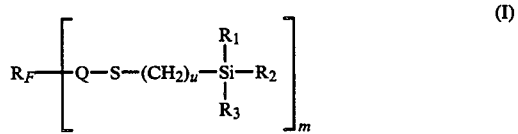

(I)

wherein $R_1$ is halogen or an alkoxy group, $R_2$ and $R_3$ are each hydrogen, a halogen, an alkoxy group, an alkyl group, or an aryl group; u is two or three; m is one or two; $R_F$ is a partially or completely fluorinated hydrocarbon; and Q is a bivalent group having at least one oxygen atom.

2. A fluorosilane according to claim 1 wherein $R_1$ and $R_2$ are chlorine or methoxy and $R_3$ is methyl.

3. A fluorosilane according to claim 1 wherein u is three.

4. A fluorosilane according to claim 1 wherein m is one.

5. A fluorosilane according to claim 1 wherein Q includes an ether group, an ester group, or an amide group.

6. A process for the preparation of a fluorosilane according to claim 1, which process comprises adding a thiosilicon group to a fluorinated olefin.

7. A process according to claim 6 wherein a silane-thiol having the formula:

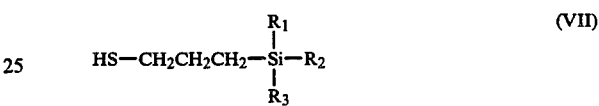

(VII)

is reacted with a fluorinated olefin having at at least one terminal end a —CH=CH$_2$ or a —CF=CF$_2$ group.

8. A process according to claim 6 wherein the reaction is carried out in an aprotic organic solvent at a temperature of from 30° to 100° C. under a nitrogen atmosphere.

9. A process according to claim 6 wherein the reaction is carried out at a temperature of from 60° to 80° C.

10. A process for the preparation of fluorinated silicones which comprises reacting the fluorosilane according to claim 1 to form a fluorinated silicone.

* * * * *